United States Patent [19]

Genna et al.

[11] Patent Number: 5,030,577
[45] Date of Patent: Jul. 9, 1991

[54] IN-LINE SAMPLING/ALLOYING SYSTEM AND METHOD

[75] Inventors: John L. Genna, Monroeville; Jeffrey B. Moreland, Pittsburgh; C. Edward Eckert, Plum Boro; Ronald E. Miller, Murrysville, all of Pa.

[73] Assignee: Aluminum Company of America, Pittsburgh, Pa.

[21] Appl. No.: 268,044

[22] Filed: Nov. 7, 1988

Related U.S. Application Data

[63] Continuation-in-part of Ser. No. 826,988, Feb. 7, 1986, Pat. No. 4,783,417.

[51] Int. Cl.$^5$ .............................................. G01N 1/10
[52] U.S. Cl. ....................................... 436/55; 436/73; 436/78; 436/171; 422/110
[58] Field of Search .................... 75/377; 422/108, 110, 422/121, 129; 436/55, 73, 78, 171, 173

[56] References Cited

U.S. PATENT DOCUMENTS

| | | | |
|---|---|---|---|
| 3,137,753 | 6/1964 | Feichtinger | 266/34 |
| 3,268,326 | 8/1966 | Harders | 75/58 |
| 3,528,800 | 9/1970 | Blum et al. | 422/108 X |
| 3,645,628 | 2/1972 | Bojic et al. | 356/86 |
| 3,659,944 | 5/1972 | Bojic | 356/86 |
| 3,669,546 | 6/1972 | Virloget | 356/86 |
| 3,672,774 | 6/1972 | Bojic et al. | 356/86 |
| 3,729,309 | 4/1973 | Kawawa | 75/129 |
| 3,768,999 | 10/1973 | Ohkubo et al. | 75/58 |
| 3,858,640 | 1/1975 | Sifferlen | 164/250 |
| 3,929,185 | 12/1975 | Wiener | 164/338 |
| 3,947,265 | 3/1976 | Guzowski et al. | 75/10 R |
| 3,963,420 | 6/1976 | Matsumoto et al. | 23/230 R |
| 3,985,031 | 10/1976 | Franz | 73/423 R |
| 4,137,774 | 2/1979 | Kumbrant | 73/425.4 R |
| 4,151,253 | 4/1979 | Waggoner et al. | 422/68 |
| 4,154,284 | 5/1979 | Maringer | 164/130 |
| 4,533,642 | 8/1985 | Kelly | 436/78 |
| 4,688,771 | 8/1987 | Eckert et al. | 266/78 |
| 4,689,199 | 8/1987 | Eckert et al. | 420/590 |
| 4,765,391 | 8/1988 | Bäckerud | 164/150 |
| 4,783,417 | 11/1988 | Genna | 436/73 |

FOREIGN PATENT DOCUMENTS

| | | | |
|---|---|---|---|
| 802133 | 12/1968 | Canada | 53/344 |
| 74024764 | 12/1970 | Japan | |
| 59-210349 | 11/1984 | Japan | |
| WO85/00884 | 2/1985 | PCT Int'l Appl. | |
| 197711 | 12/1977 | U.S.S.R. | |
| 1116052 | 6/1968 | United Kingdom | |

Primary Examiner—Charles Hart
Attorney, Agent, or Firm—Gary P. Topolosky

[57] ABSTRACT

A system for in-line alloying of a molten metal stream comprises: means for controlling mass flow rate of the stream; means for adding alloying material to the stream at an adjustable rate; means for determining chemical composition of the stream downstream from the material adding means, preferably at timed intervals; and means for adjusting the rate at which alloying material is added to the stream based on mass flow rate and the extent to which the determined stream composition differs from a desired composition. A method for conducting in-line alloying and analysis of a continuous metal stream is also disclosed.

20 Claims, 2 Drawing Sheets

IN-LINE SAMPLING/ALLOYING SYSTEM AND METHOD

This is a continuation-in-part of application Ser. No. 06/826,988, filed on Feb. 7, 1986, U.S. Pat. No. 4,783,417 the disclosure of which is fully incorporated by reference herein.

BACKGROUND OF THE INVENTION

1. Field of the Invention

This invention relates to an in-line system for sampling and adding alloying materials to a molten metal stream. The invention further relates to a method for alloying and analyzing a continuous metal stream at precise time intervals. With the present invention, castings may be changed from one alloy composition to another "on the fly", or with no substantial interruption of the basic casting process.

When continuously casting most molten metal alloys, production inefficiencies result from the need to periodically determine whether a molten composition falls within a preferred target range. Ideally, compositions should be monitored on a substantially continuous basis to assure greater uniformity in cast product. Efficiencies are further reduced when any variation from the targeted composition range occurs. Until such variations are detected and corrected, they will produce substantial quantities of undesirable metal alloy or scrap. The present invention increases casting efficiencies while also reducing the amount of scrap generated by continuous metal casting operations.

2. Technology Review

Various methods are known for analyzing or sampling cast alloys while still molten. In its simplest form, molten metal sampling may consist of removing a sufficient portion of the melt and sending it out for spectral analysis. Distant laboratory analyses produce unacceptable lags in casting time, however. Direct spectral analysis of molten metals, on the other hand, creates problems from the need to locate sensitive spectrometry equipment in immediate proximity to the casting furnaces.

An exemplary system for sampling molten metals, such as aluminum alloys, is shown in related application Ser. No. 06/826,988, the disclosure of which, including its discussion of the relevant art, is fully incorporated by reference herein. In the integrated system of this related application, a preferred method for analyzing molten metal samples is disclosed which comprises: (a) removing sample metal as a solid from a source of molten metal by immersing serrations of a rotating disc into the melt; (b) transporting the sample metal from the rotating disc to a dissolution zone; (c) dissolving the sample metal in a solvent to form dissolved sample in the dissolution zone; (d) passing the dissolved sample from the dissolution zone to an emission spectrometer; (e) vaporizing the dissolved sample in the spectrometer; (f) producing an emission spectra for the vaporized sample; and (g) comparing the emission spectra of the vaporized sample to that of a known alloy thereby determining the composition of said vaporized sample.

There is also known means by which to add alloying elements, materials or other components to a molten metal media. Eckert et al U.S. Pat. Nos. 4,688,771 and 4,689,199, for example, show a system and process for alloying certain materials to molten metal at a commercially significant rate. A preferred alloying process from the latter patent comprises: providing a body of molten metal media having an exterior and an interior surface; converting the alloying material into a superheated spray by establishing an electrical arc discharge between the interior surface of the molten media and the alloying material, said discharge being maintained with a current that exceeds the globular/spray transition current density of the alloying material; and directing the spray of superheated alloying material onto the interior media surface so as to enable dissolution and dispersion of the material into the media, the interior surface of said media being maintained a predetermined depth below the exterior surface which is sufficient for enhancing dissolution and dispersion. The disclosures of both U.S. patents, including their respective discussions of the relevant art, are also fully incorporated by reference herein.

In U.S. Pat. No. 4,765,391, there is shown an arrangement for effecting thermal analysis and molten metal modification by recording solidification data and controlling a subsequent structure-modifying process on the basis of the data obtained. The claimed arrangement consists of: a sampling container constructed such that molten metal fills the container upon immersion into the melt; means for effectively measuring and recording solidification data from one or more locations of the sample obtained with said container; means for evaluating this solidification data relative to data from a melt having a known metallurgical structure; means for controlling the supply of molten metal additions, or for subjecting the molten metal to structure-modifying measures in a controlled manner; and control means for continuously monitoring structure-modifying measures by sampling the molten metal intermittently at suitable time intervals.

SUMMARY OF THE INVENTION

It is a principal object of the present invention to provide a system for in-line alloying a molten metal stream. It is a further object to provide a substantially continuous alloying and analyzing system which modifies material addition rates based on mass flow rate and preceding emission spectra comparisons versus a desired composition. It is a further object to provide an in-line system with the ability to anticipate or better predict when to adjust material addition rates, said system including a closed loop-feedback control. It is a further object to provide alloying systems which account for substantial melt homogenizations before or after repeated compositional samplings.

It is another object of this invention to provide a method for conducting in-line analysis and alloying of a continuous metal stream. The invention further provides means for casting multiple product compositions from the same base metal stream by varying the amount of alloying material being added to the stream.

In accordance with the foregoing objects and advantages, there is disclosed a system for in-line alloying of a molten metal stream which comprises: means for monitoring mass flow rate of the stream; means for adding alloying material to the stream; means for determining chemical composition downstream from the material adding means, preferably at timed intervals; and means for adjusting the amount of alloying material added to the stream based on mass flow rate and the determined chemical composition relative to a desired metal composition. There is further disclosed a method for conducting in-line alloying and analysis of a continuous metal stream.

BRIEF DESCRIPTION OF THE DRAWINGS

Further features, other objects and advantages of this invention will become clearer from the following detailed description of the preferred embodiments made with reference to the drawings in which.

DETAILED DESCRIPTION OF THE PREFERRED EMBODIMENTS

Figure 1:
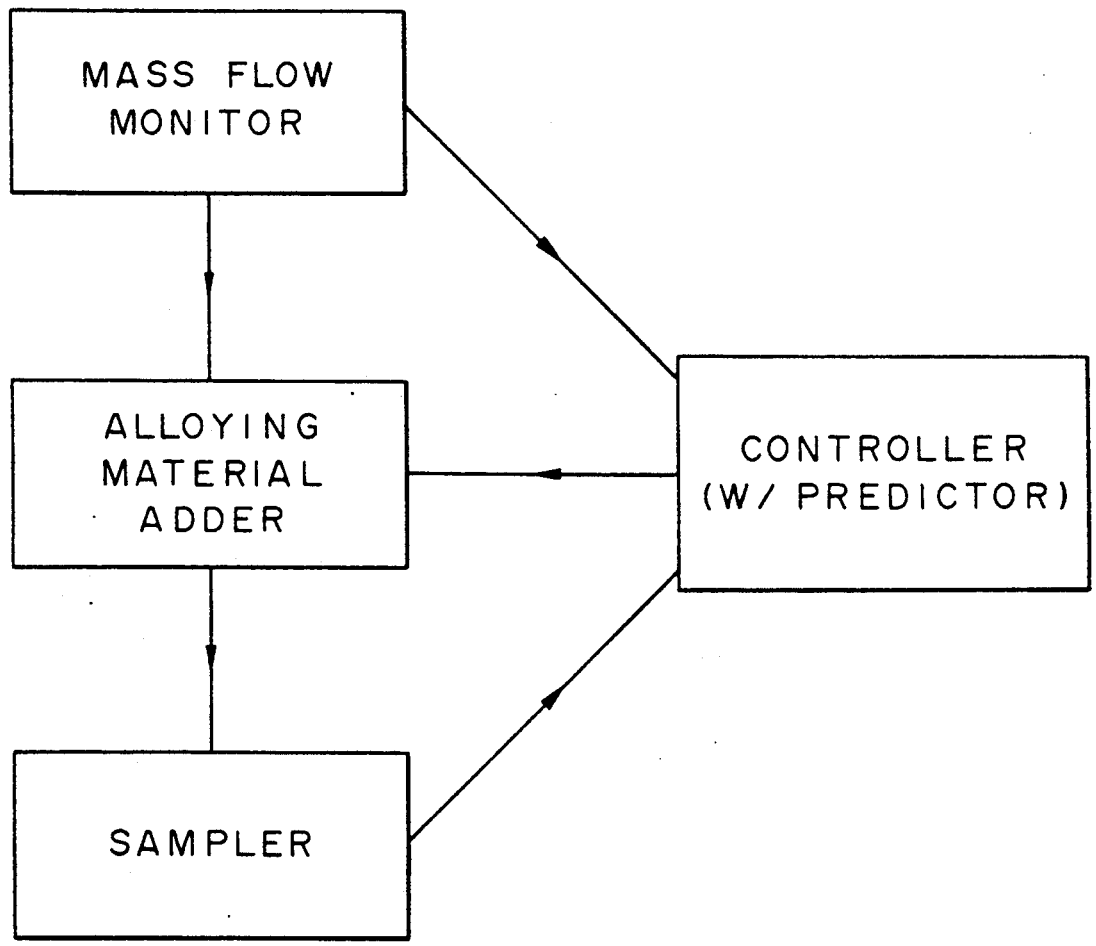
FIG. 1 is a flow sheet illustrating the system of this invention.

As depicted in the flow sheet at FIG. 1, the system of this invention includes means for monitoring, measuring, approximating or otherwise controlling the mass flow rate of a molten metal stream being alloyed. By controlling, it is meant that mass flow may be varied by a known amount, or maintained at a substantially constant or uniform rate. The system further includes means for adding alloying material, or components, to the stream at an adjustable or variable rate which is commercially significant. Another system element includes means for periodically sampling the molten metal stream, preferably at precisely timed intervals. Each of the foregoing system elements then interrelates with a common controller as shown by the directional arrows between flow sheet boxes in FIG. 1. Both the mass flow monitor and sampler provide input to the controller which converts these signals into a feedback means for varying or adjusting the rate at which further alloying material is added upstream of the sampling means. In other words, the controller of this closed loop system either lowers, raises or maintains a constant material addition rate based on the stream mass flow rate (especially when mass flow is not kept uniform), and on the extent to which samples of actual stream composition vary from a desired, target or otherwise known composition.

The controller of FIG. 1 is parenthetically shown with an optional predictor or system modelling means. With a predictor, the system of this invention is better able to gauge, estimate or anticipate when changes to the material addition rate might be needed. Should the predictor's estimations compare favorably with actual system observations, a predictor-enhanced system may better react to avoid otherwise long processing delays. For this invention, two types of predictors have been coupled with a preferred controller. A modified Broner prediction-controller combination exhibited improved response times with more rapid disturbance rejections while a Smith predictor-enhanced controller produced better zero steady state error control.

Figure 2:
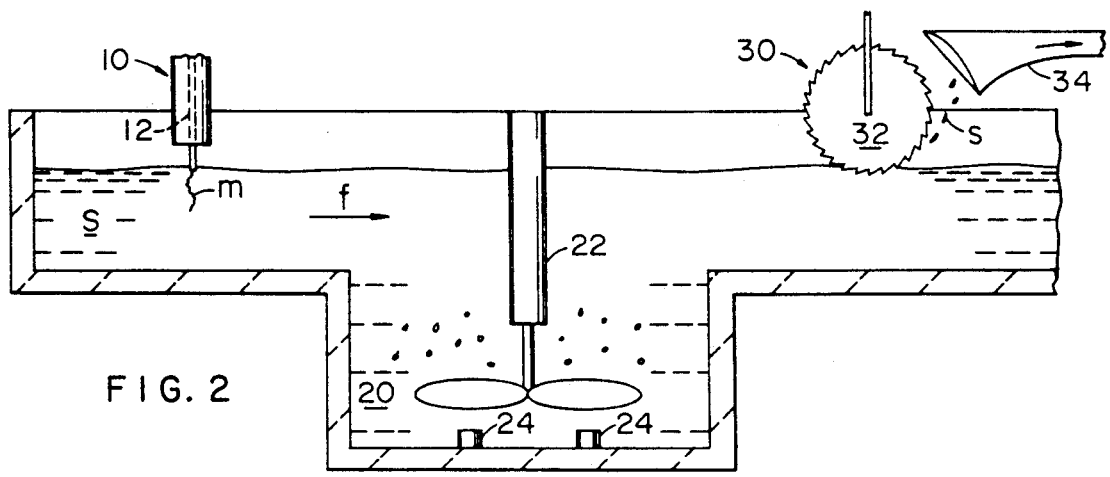
FIG. 2 is a schematic side view of a first preferred embodiment of this system.
Figure 3:
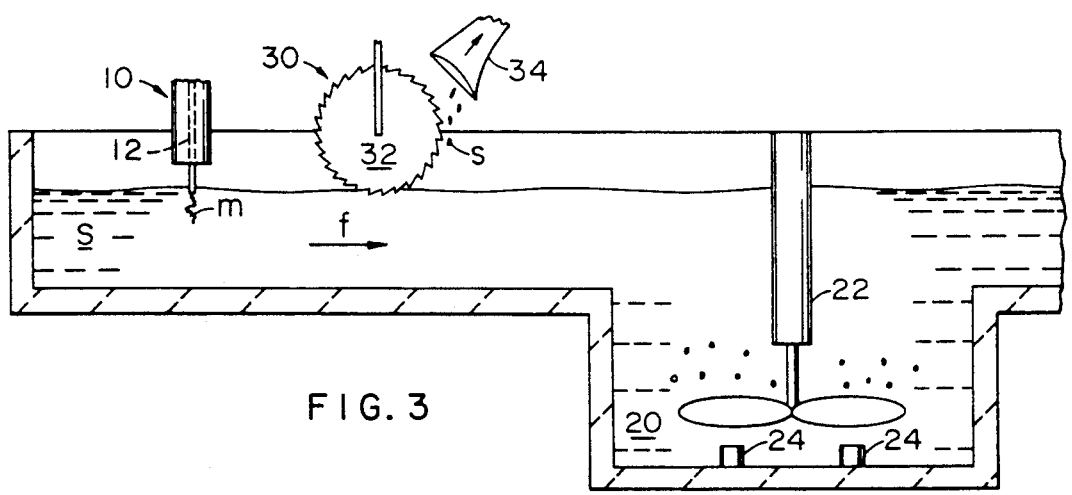
FIG. 3 is a schematic side view of a second preferred embodiment.
Figure 4:
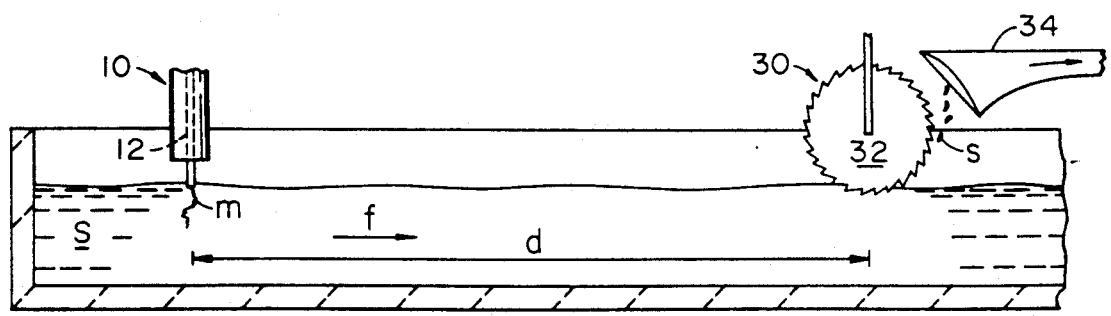
FIG. 4 is a schematic side view of a third preferred embodiment.

Referring now to FIGS. 2-4, there is schematically shown several preferred embodiments of the invention. Within the respective side views of a continuous molten metal processing stream, system elements having equivalent structures in more than one embodiment are correspondingly numbered. In FIG. 2, alloying material addition means, generally 10, is shown as part of a plasma arc alloying device. This device consists of an elongate chamber 12 having a lower end exposed to molten metal stream S at a substantial depth, said stream having a directional flow as indicated by arrow f therein. Chamber 12 also includes an upper end, at least a portion of which is located above the exterior surface of stream S. Other structural aspects of this exemplary plasma arc device have been deleted from the accompanying drawings for simplified illustration purposes. Nevertheless, such devices typically consist of: means for supplying alloying material m to chamber 12 through its upper end; means for conducting an electrical arc and maintaining a plasma within the chamber, said plasma extending from an interior surface of stream S to the material m being supplied; means for feeding material m into the plasma and conducting it to the interior surface of stream S; and means for substantially continuously feeding gas into chamber 12, and pressurizing said gas from the lower chamber end thereby projecting material m through the interior stream surface and into the melt. It is to be understood that the foregoing plasma arc alloying device is merely exemplary of one preferred embodiment for adding alloying material to the system of this invention. Should more particulars about a plasma arc-type material adding means be desired, please refer to Eckert et al U.S. Pat. Nos. 4,688,771 and 4,689,199, the disclosures of which are fully incorporated by reference herein.

To the immediate right of material adding means 10 in FIG. 2, there is located a homogenization zone 20. Within this zone, stirrer 22 significantly contributes to the dispersion and dissolution of alloying material throughout the entire molten metal stream S. Zone 20 further includes aeration ports 24 through which argon, chlorine and/or other gases may be bubbled for melt-fluxing purposes. Although stream purity levels and homogeneity are significantly improved when a zone 20 is incorporated into the present invention, these homogenization zones also have a detrimental effect on system response or reaction time. The larger zone 20 is relative to the rest of stream S, the longer it will take to detect changes in alloy composition with the sampler means 30 of this system, unless, of course, sampler 30 is positioned before the homogenization zone as in the second preferred embodiment at FIG. 3.

One preferred embodiment of chemical composition determining means, according to this invention, consists of a solid sampler 30 and its related analytical equipment (not shown). With proper positioning and calibration of a relatively rapid composition determining means, this invention is able to periodically compare the composition of stream being substantially continuously cast with that of a desired or target composition. Following each compositional comparison, the system is designed to loop back and correct for any variations from the target by modifying or adjusting the rate at which additional alloying material is being added upstream of sampler 30. With an added predictor, or modelling mechanism, the system may be made to better react or respond to any compositional variations which are detected.

The chemical composition determining means for the embodiments illustrated at FIGS. 2-4 consists of: sampler 30, or means for removing metal samples s from stream S as a solid; means for dissolving samples s in a suitable solvent for emission spectrometry analysis; means for producing an emission spectra for the dissolved samples s; and means for comparing the samples' emission spectra with that of a desired composition. Sampler 30, itself, consists of a rotating wheel 32 having immersible serrations which contact with the molten metal stream S to produce solid particles or flakes of metal samples s. Such samples are then transported, by suction tube 34, to a location remote from the molten metal furnace for compositional analysis. (An exemplary sampler of this sort is shown and described in application Ser. No. 06/826,988, the disclosure of which is fully incorporated by reference herein.) At this remote location, the metal samples s are rapidly dissolved in a suitable solvent, vaporized and subjected to emission spectrometry analysis. Alternatively, the samples could be subjected to other currently existing or subsequently developed analytical means.

In the third preferred embodiment depicted at FIG. 4, a homogenization zone has been removed from the system. By eliminating of any sort of holding area from the continuous casting stream, there will naturally be more rapid detection of compositional changes. For this particular embodiment, therefore, mass flow rate measurements have even greater importance while the distance d between alloying means 10 and sampler 30 also becomes critical. Particularly, the greater extent to which distance d is reduced, the shorter the response time to detect and correct for any casting composition variations from one or more target ranges.

The preceding detailed description does not limit application of this system to any particular metal or metal alloy. On a preferred basis, this system and method is used to monitor the continuous casting of substantially pure aluminum or aluminum alloys containing a predetermined amount of alloying material. For example, if the system is set up to monitor the casting of an aluminum alloy containing 5% magnesium, the starting melt may be pre-alloyed with as much as 2 or 3% magnesium. It is to be understood, however, that the invention is not limited to aluminum-based alloys, magnesium additions, or single element additions for that matter. Rather, the invention may be used to cast most other metal alloys, including magnesium or steel. It may also be used to add to a molten metal stream such other alloying materials as copper, zinc, iron, manganese, lead, bismuth, silicon, nickel, chromium, boron, titanium, zirconium, vanadium, strontium, lithium and any mixtures thereof, said mixtures being meant to include alloys, compounds or any other combinations thereof. It is to be further understood that the system of this invention may also be used to add to a molten metal stream still other alloying materials than those listed above. The present invention may also be used to monitor the transition from one preferred casting composition to another.

Having described the presently preferred embodiments, it is to be understood that the present invention may be otherwise

What is claimed is:

1. A system for in-line alloying of a molten metal stream which comprises:
   means for monitoring mass flow rate of the stream and generating a first signal representative of said mass flow rate,
   means for adding alloying material to the stream,
   means for determining the chemical composition of said stream and generating a second signal representative of said chemical composition, and
   a controller for receiving the first and second signals, comparing the second signal against that of a desired chemical composition and adjusting the rate at which alloying material is added to the stream from the material adding means based on the first and second signals.

2. A system as set forth in claim 1 which includes means for substantially homogenizing the stream prior to determining the chemical composition thereof.

3. A system as set forth in claim 1 wherein the composition determining means is positioned downstream from the material adding means.

4. A system as set forth in claim 1 wherein the material adding means includes:
   an elongate chamber having a lower end which can be exposed to the molten metal stream at a substantial depth, and an upper end, at least a portion of which is located above an exterior surface of the stream,
   means for supplying alloying material to the chamber through its upper end,
   means for conducting an electrical arc and maintaining a plasma within the chamber, said plasma extending from an interior surface of the stream to the alloying material being supplied,
   means for feeding alloying material into the plasma and conducting it to the interior surface of the stream, and
   means for substantially continuously feeding gas into the chamber and pressurizing said gas from the lower chamber end in order to project alloying material through the interior surface of the stream.

5. A system as set forth in claim 1 wherein the composition determining means includes:
   means for periodically removing metal samples from the stream as a solid,
   means for dissolving said metal samples in a solvent suitable for emission spectrometry analysis,
   means for producing an emission spectra for said metal samples.

6. A system for substantially continuously adding alloying material to a molten metal stream, periodically analyzing said stream for its alloying material content, and adjusting the amount of alloying material being added to said stream responsive to its periodic analysis, said system comprising:
   means for measuring the mass flow rate of the stream,
   means for adding alloying material to the stream at an adjustable rate,
   means for removing metal samples from the stream a known distance apart from the material adding means,
   means for transporting the metal samples to an emission spectrometer for compositional analysis,
   means for comparing the compositional analysis of the metal samples with a target metal composition, and
   means for adjusting the rate at which alloying material is added to the stream responsive to: the mass flow rate of the stream, the distance between the sample removing means and material adding means, and the comparison of metal sample composition versus target composition.

7. A system as set forth in claim 6 wherein the material adding means consists essentially of a plasma arc alloying device.

8. A system as set forth in claim 6 wherein the molten stream consists essentially of aluminum and the alloying material is selected from: magnesium, copper, zinc, iron, manganese, lead bismuth, silicon, nickel, chromium, boron, titanium, zirconium, vanadium, strontium, lithium and mixtures thereof.

9. A system as set forth in claim 6 wherein the sample removing means is positioned downstream from the material adding means.

10. An in-line system for adding alloying material to a molten metal stream to produce metal products having a substantially uniform composition throughout, said system comprising:
   means for determining mass flow rate of the stream,
   a plasma arc alloying device for adding alloying material to the stream at an adjustable rate,
   means for homogenizing the stream,
   means for removing solid metal samples from the stream,
   means for analyzing the chemical composition of said metal samples through emission spectrometry,
   means for comparing the emission spectra of said metal samples with that for a target alloy composition, and
   means for adjusting the rate at which alloying material is added to the stream responsive to its mass flow rate and the comparison of sample versus target emission spectra.

11. A system as set forth in claim 10 which further includes:
   means for modelling the system to predict when variations in composition will occur so as to reduce response time to said variations.

12. A system as set forth in claim 10 wherein the molten metal stream consists essentially of substantially pure aluminum.

13. A system as set forth in claim 10 wherein the molten metal stream consists essentially of aluminum and a predetermined amount of the alloying material.

14. A system as set forth in claim 10 wherein the alloying material is selected from magnesium, copper, zinc, iron, manganese, lead, bismuth, silicon, nickel, chromium, boron, titanium, zirconium, vanadium, strontium, lithium and mixtures thereof.

15. A system as set forth in claim 10 wherein the sample removing means is positioned a known distance downstream from the plasma arc alloying device.

16. A method for conducting in-line alloying and analysis to control the chemical composition of a substantially continuous molten metal stream, said method comprising:
   monitoring the mass flow rate of the stream,
   adding alloying material to the stream at an adjustable rate,
   periodically sampling the stream for determining its chemical composition,
   comparing the chemical composition of the samples with that of a target composition, and
   adjusting the rate at which alloying material is added to the stream responsive to its mass flow rate and the extent to which chemical composition of the samples differs from the target composition.

17. A method as set forth in claim 16 wherein the chemical composition of the stream is sampled downstream from where alloying material is added.

18. A method as set forth in claim 16 wherein the molten metal stream consists essentially of aluminum.

19. A method as set forth in claim 16 wherein the alloying material is selected from magnesium, copper, zinc, iron, manganese, lead, bismuth, silicon, nickel, chromium, boron, titanium, zirconium, vanadium, strontium, lithium and mixtures thereof.

20. A method for in-line casting molten aluminum having a substantially uniform chemical composition, said method comprising:
   providing a substantially continuous stream of molten aluminum,
   monitoring the mass flow rate of the stream,
   adding alloying material to the stream at an adjustable rate,
   periodically removing solid samples from the stream,
   performing emission spectra analysis on the samples to determine the chemical composition of said stream downstream from where alloying material is being added thereto,
   comparing the chemical composition of the stream with that of a target composition, and
   adjusting the rate at which alloying material is being added to the stream responsive to its mass flow rate and the comparison of sample versus target chemical compositions.

* * * * *